United States Patent [19]

Viegas et al.

[11] Patent Number: 5,593,683

[45] Date of Patent: Jan. 14, 1997

[54] METHOD OF MAKING THERMOREVERSIBLE POLYOXYALKYLENE GELS

[75] Inventors: Tacey X. Viegas, Canton; Lorraine E. Reeve, Dexter; Raymond L. Henry, St. Clair Shores, all of Mich.

[73] Assignee: MDV Technologies, Inc., Dearborn, Mich.

[21] Appl. No.: 205,305

[22] Filed: Mar. 3, 1994

Related U.S. Application Data

[63] Continuation-in-part of Ser. No. 759,234, Sep. 13, 1991, Pat. No. 5,300,295, Ser. No. 895,949, May 9, 1992, Pat. No. 5,298,260, Ser. No. 791,119, Nov. 8, 1991, Pat. No. 5,306,501, and Ser. No. 790,664, Nov. 8, 1991, Pat. No. 5,292,516, which is a continuation-in-part of Ser. No. 517,273, May 1, 1990, abandoned, said Ser. No. 759,234, is a continuation-in-part of Ser. No. 517,273, May 1, 1990, abandoned, said Ser. No. 895,949, May 9, 1992, is a continuation-in-part of Ser. No. 517,282, May 1, 1990, abandoned, said Ser. No. 791,119, Nov. 8, 1991, is a continuation-in-part of Ser. No. 517,277, May 1, 1990, abandoned.

[51] Int. Cl.⁶ ............................. A61K 9/10; A61K 47/34
[52] U.S. Cl. ......................... 424/427; 424/486; 514/944; 514/912; 523/105; 523/122; 252/315.1
[58] Field of Search .................... 424/427, 486; 514/944, 954, 912–915, 772.1; 523/109, 111, 122; 252/315.1

[56] References Cited

U.S. PATENT DOCUMENTS

| | | | |
|---|---|---|---|
| 2,677,700 | 5/1954 | Jackson et al. | 260/488 |
| 3,036,118 | 5/1962 | Jackson et al. | 260/484 |
| 3,535,307 | 10/1970 | Moss et al. | 260/209 |
| 3,590,125 | 6/1971 | Hymes | 424/78 |
| 3,829,506 | 8/1974 | Schmolka et al. | 260/615 |
| 3,867,521 | 2/1975 | Miskel | 424/37 |
| 4,100,271 | 2/1976 | Krezanoski | 424/78 |
| 4,185,618 | 1/1980 | Corey | 128/1 R |
| 4,188,373 | 2/1980 | Krezanoski | 424/78 |
| 4,255,415 | 3/1981 | Chrai et al. | 424/78 |
| 4,439,196 | 3/1984 | Higuchi | 604/890 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,511,563 | 4/1985 | Schmolka | 514/162 |
| 4,534,958 | 8/1985 | Adams et al. | 424/45 |
| 4,767,619 | 8/1988 | Murray | 424/78 |
| 4,810,503 | 3/1989 | Carson et al. | 424/763 |
| 4,861,760 | 8/1989 | Mazuel et al. | 514/54 |
| 4,879,109 | 11/1989 | Hunter | 424/83 |
| 4,883,660 | 11/1989 | Blackman et al. | 424/78 |
| 4,911,926 | 3/1990 | Henry et al. | 424/426 |
| 5,017,370 | 5/1991 | Hunter et al. | 424/83 |
| 5,030,448 | 7/1991 | Hunter | 424/83 |
| 5,068,225 | 11/1991 | Pennell et al. | 514/57 |
| 5,292,516 | 3/1994 | Viegas et al. | 424/423 |
| 5,298,260 | 3/1994 | Viegas et al. | 424/486 |
| 5,300,295 | 4/1994 | Viegas et al. | 424/427 |
| 5,306,501 | 4/1994 | Viegas et al. | 424/423 |

FOREIGN PATENT DOCUMENTS

| | | |
|---|---|---|
| 0065385A2 | 11/1982 | European Pat. Off. . |
| 0386960 | 2/1990 | European Pat. Off. . |
| 0517160 | 2/1992 | European Pat. Off. . |
| 2336945 | 7/1977 | France . |
| 61-277612 | 12/1986 | Japan . |
| 1554783 | 10/1979 | United Kingdom . |
| 1571832 | 7/1980 | United Kingdom . |
| 2105991 | 4/1983 | United Kingdom . |
| WO86/00813 | 2/1986 | WIPO . |

OTHER PUBLICATIONS

Lampert and Williams (1972), *J. of Biomed. Mater. Res.*, vol. 6, pp. 499–532.

Kim, et al., "Pluronic® Polyol: A Potential Alloplastic Keratorefractive Material"; Journal of Cataract Refractive Surgery, vol. 14, May 1988, pp. 312–316.

*Primary Examiner*—Edward J. Webman
*Attorney, Agent, or Firm*—Banner & Witcoff, Ltd.

[57] ABSTRACT

Compositions based upon aqueous gels for medical application, comprising polyoxyalkylene copolymers. Such gels which are isotonic, iso-osmotic, pH balanced, thermo-reversible gels are ideal vehicles for drug or diagnostic agent delivery.

2 Claims, 1 Drawing Sheet

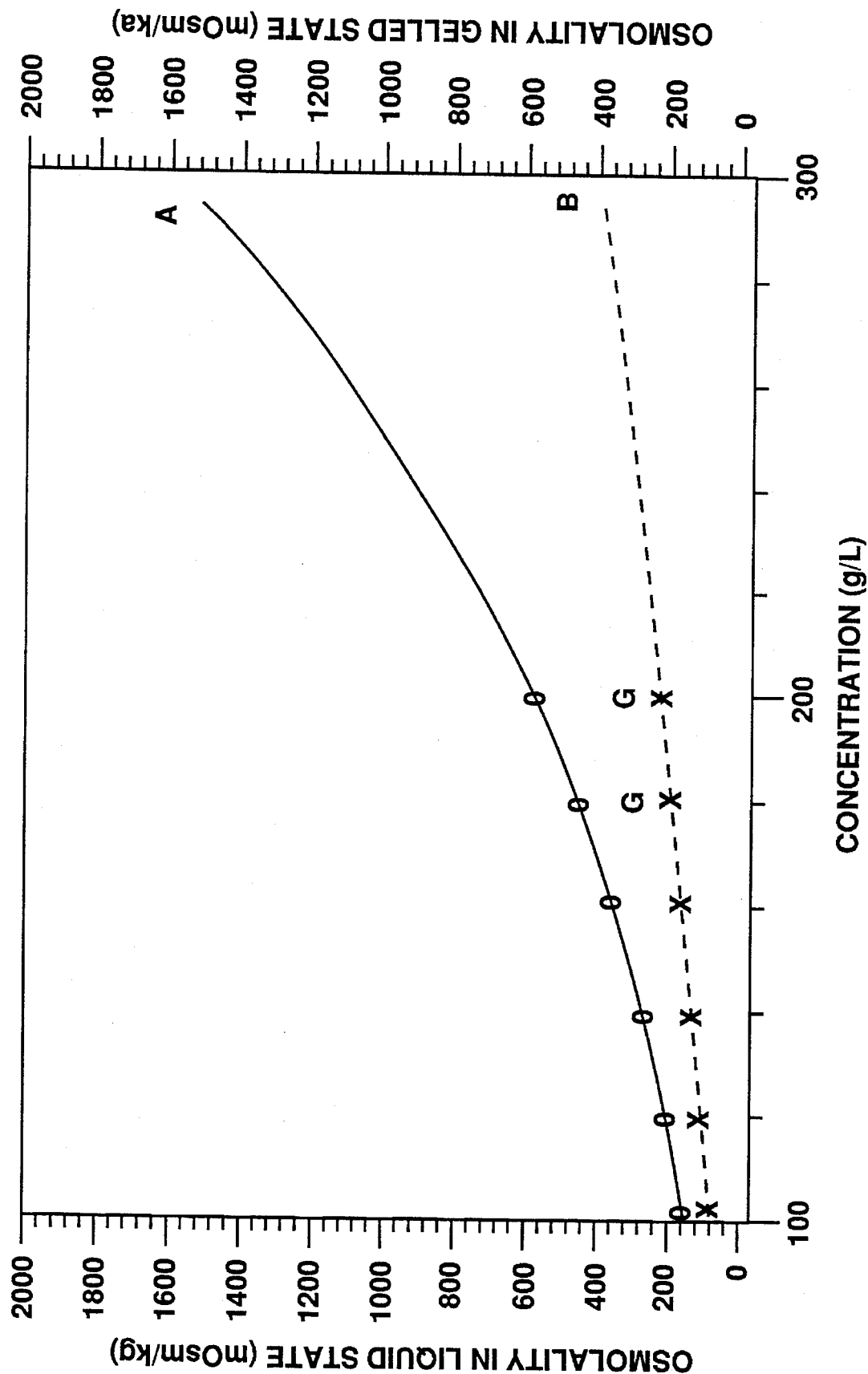

METHOD OF MAKING THERMOREVERSIBLE POLYOXYALKYLENE GELS

This application is a continuation-in-part of the following U.S. patent applications: Ser. No. 07/759,234, filed Sep. 13, 1991, entitled "Ophthalmic Drug Delivery with Thermoreversible Polyoxyalkylene Gels Adjustable for pH and Osmolality" (assigned to the assignee of the present invention and the entire disclosure of which is incorporated herein by reference) now U.S. Pat. No. 5,300,295; Ser. No. 07/895,949, filed May 9, 1992, entitled, "Topical Drug Delivery with Polyoxyalkylene Polymer Thermoreversible Gels Adjustable for pH and Osmolality" (assigned to the assignee of the present invention and the entire disclosure of which is incorporated herein by reference) now U.S. Pat. No. 5,298,260; Ser. No. 07/791,119, filed Nov. 8, 1991, entitled "Drug Delivery by Injection with Thermoreversible Gels Adjustable for pH and Osmolality" (assigned to the assignee of the present invention and the entire disclosure of which is incorporated herein by reference) now U.S. Pat. No. 5,306,501; Ser. No. 07/790,664, filed Nov. 8, 1991, entitled "Body Cavity Drug Delivery with Thermoreversible Gels" (assigned to the assignee of the present invention and the entire disclosure of which is incorporated herein by reference) now U.S. Pat. No. 5,292,516; which are respectively, continuation-in-part Applications of the following U.S. Patent Applications, now abandoned: Ser. No. 07/517,273 (filed May 1, 1990); Ser. No. 07/517,282 (filed May 1, 1990); Ser. No. 07/517,277 (filed May 1, 1990), and Ser. No. 07/517,278 (filed May 1, 1990).

FIELD OF THE INVENTION

The present invention relates to compositions based on aqueous gels and their particular use in delivery systems for drugs or diagnostic agents.

BACKGROUND OF THE INVENTION

Over the years, methods have been developed to achieve the efficient delivery of a therapeutic drug to a mammalian body part requiring pharmaceutical treatment. Use of an aqueous liquid which can be applied at room temperature as a liquid but which forms a semisolid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In the U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum, below which a gel will not form.

In U.S. Pat. Nos. 4,474,751; '752; '753; and 4,478,822 drug delivery systems are described which utilize thermosetting gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; and 4,861,760. Thermosetting gel systems are also disclosed for application to injured mammalian tissues of the thoracic or peritoneal cavities in U.S. Pat. No. 4,911,926.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, kpro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Compositions and a process are disclosed for pharmaceutical compositions generally containing pharmacologically active medicaments which are useful in providing treatments to areas of the mammalian body requiring pharmacological treatment or, alternatively, requiring the administration of a diagnostic agent. The pharmaceutical compositions in one embodiment of the invention provide a physiologically acceptable medium having a buffered pH and an osmotically balanced vehicle, generally characterized as hyper-osmotic, iso-osmotic, or hypo-osmotic. Preferably, an isotonic mixture is provided which is iso-osmotic with body fluids and has a buffered pH similar to bodily fluids, such as lacrimal tears. The pH and osmotic pressure of lacrimal tears are about pH 7.4 and 290 mOsm/kg respectively. In addition, the pharmaceutical compositions are, optionally, sterilized so as to insure that the pharmaceutical compositions of the invention do not provide a source of infection. The compositions of the present invention can be adjusted to the desired osmolality by assuming that a polyoxyalkylene block copolymer present therein does not contribute to the osmolality and, therefore, to the osmotic force, in the gel state.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

In a preferred embodiment, the compositions of the invention can be delivered to the area of the mammalian body requiring treatment as a low viscosity liquid at ambient temperatures which, upon contact with the mammalian body, forms a semi-solid gel having a very high viscosity. Because the preferred pharmaceutical compositions of the invention are low viscosity liquids at ambient temperatures, they easily pass to various ophthalmic areas insuring maximum contact between exposed tissue and the pharmaceutical composition of the invention. If necessary, the preferred pharmaceutical compositions of the invention can be washed away under a gentle stream of cool water, thus minimizing the risk of further injury and pain to the patient upon removal.

A wide variety of polyoxyalkylene polymers are suitable for the preparation of the pharmaceutical compositions of the invention. Generally, it is necessary to adjust the polymer concentration in aqueous solution so as to obtain the desired sol-gel transition temperature in order that the compositions can be provided as low viscosity liquids at ambient temperature, yet form semi-solid gels at mammalian body temperatures. In addition to the concentration of the polymer and the concentration of a water soluble or dispersible pharmacologically active medicament, other suitable excipients must be added so as to provide the preferred isotonic, iso-osmotic properties (i.e., iso-osmotic, hyperosmotic, or hypo-osmotic).

BRIEF DESCRIPTION OF THE DRAWING

The drawing provides a curve showing the osmolality in the solution state of a polyoxyalkylene copolymer, identified as Poloxamer 407, at various concentrations in a 0.1 molar TRIS hydrochloride buffer. The scale at the left side of the plot indicates the osmolality in the liquid state, while the scale on the right side of the plot indicates the osmolality of the composition when in the gelled state, assuming that the gelled Poloxamer 407 molecules no longer contribute to the osmotic force. Thus, curve A provides a graph showing the osmolality calculated for the gel state. Curve A is obtained by measuring the effect upon the freezing point depression of the Poloxamer 407 solutions in comparison with a sample of purified water (deionized water). It is noted that the curves were obtained by fitting the osmolality and concentration of polymer to the quadratic equation, $Y=A+Bx+Cx^2$, where Y is osmolality, x is concentration, and A, B, and C are constants. The relationship of concentration to osmolality is nonlinear in this system.

DETAILED DESCRIPTION OF THE PREFERRED EMBODIMENTS

It has been found that aqueous pharmaceutical vehicles containing a polyoxyalkylene block copolymer, which have the unique feature, in a preferred embodiment, of being liquid at ambient temperatures and transitioning at mammalian body temperatures to a semi-solid gel, can be made isotonic or iso-osmotic in the gel state and can be buffered to the pH of mammalman body fluids, such as lacrimal tears. The pH and osmotic pressure of such bodily fluids are 7.4 and 290 mOsm/kg, respectively. It is, accordingly, advantageous to deliver a pharmacologically active medicament in gel form or in liquid form, which converts to a gel at mammalian body temperatures. The area of the mammalian body requiring pharmacological treatment is, thus, treated with a gel composition having pH and osmotic pressure characteristics which match those of bodily fluids. Optionally, the pharmaceutical compositions of the invention can be provided in a sterile condition.

In addition to those well-known polyoxyalkylene block copolymers described below which are suitable in the formation of the pharmaceutical compositions of the invention, other less well-known polyoxyalkylene polymers, which form gels at low concentrations in water, are suitable. One such polymer is described in U.S. Pat. No. 4,810,503, the entire disclosure of which is incorporated herein by reference. These polymers are prepared by capping conventional polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactants, which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers. Ethylene oxide homopolymers capped with said alpha-olefin oxides are also useful as intermediates.

The heretic copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxide having from 3 to 4 carbon atoms are used in said intermediates in amounts so that the resulting polyether product will contain at least 10 percent, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heretic copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, and preferably about 20 to 30, carbon atoms. The amount of alpha-olefin required to obtain the more efficient capped polyethers is generally about 0.1 to 10 percent, and preferably about 4 to 8 percent, of the total weight of the polyethers.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, the entire disclosure of which is incorporated herein by reference. Further information on the preparation of block copolymers of lower alkylene oxides can be obtained in U.S. Pat Nos. 3,535,307; 3,036,118; 2,979,578; 2,677,700; and 2,675,619, the entire disclosures of which are incorporated herein by reference.

The surfactants may be ionic or non-ionic and many surfactants and types of surfactants may be employed. While all surfactants may not be effective in the preparation of the isotonic gels of the instant invention, the fact that many are effective makes it a simple matter for one skilled in the art to select such surfactants with a minimum of trial and error.

The amounts of capped polyether polymer and surfactant used in the aqueous compositions of the invention may be as little as 1.0 percent by weight or less for example 0.01, of each depending on the type and amount of the other component. There appears to be no maximum amount of either component than that dictated by economic considerations. However, the total amount of capped polymer and surfactant would generally not exceed 10 percent by weight.

With specific reference to the use of the pharmaceutical compositions as ophthalmic drug delivery compositions, it is noted that for the avoidance of adverse physiological effects to the eye, it is desirable that the pH and osmolality of the pharmaceutical vehicle be matched to the pH and osmolality of the eye. In addition, it is noted that a large percentage of drugs administered to the eye are lost as a result of lacrimal drainage. This applies especially in situations in which a liquid composition containing a pharmacologically active medicament is applied to the cornea of the eye. Accordingly, in such cases, only a small fraction of the pharmaceutical composition administered to the eye remains in contact with the cornea for a few minutes and an even smaller fraction penetrates into the cornea. To overcome these disadvantages, it is known to use viscous solutions, gels, ointments, or solid eye implants containing pharmacologically active medicaments. While progress has been made in the delivery of drugs by the use of solid implants, many patients find it difficult to tolerate the introduction of the implants into the conjunctival areas.

To solve this problem, drug delivery systems which are liquid at room temperature and assume a semi-solid form at human body temperature have been proposed, such as those described in U.S. Pat. No. 4,188,373, which disclose the use of PLURONIC® polyols. In U.S. Pat. No. 4,861,760 and U.S. Pat. No. 4,474,751, ophthalmic drug delivery systems are disclosed which show liquid-gel phase transitions. In the '751 Patent, polymers are disclosed which are tetra substituted derivatives of ethylenediamine, propylenediamine, butylenediamine, pentylenediamine, or hexylenediamine. These are described as block copolymers of poly(oxypropylene) and poly(oxyethylene) of various chain lengths. These polymers are described for use in aqueous drug delivery vehicles, which contain from 10% to 50% by weight of copolymer based on the weight of the total drug delivery vehicle.

In the '760 Patent, referred to above, the liquid-gel phase transition compositions for ophthalmological use contain polymers which form gels at concentrations 10–100 fold lower than those used in systems such as the '751 Patent, involving thermogellation. Accordingly, the drug delivery systems of the '760 Patent are said to be very well tolerated by the eye. The polymers utilized in the drug delivery vehicles of the '760 Patent are described as polysaccharides obtained by fermentation of a microorganism.

Generally, the polyoxyalkylene block copolymers of the invention are defined as follows:

a polyoxyalkylene block copolymer of the formula $$Y[(A)_n-E-H]_x \tag{I}$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the copolymer, n has a value such that the average molecular weight is at least about 500, as determined by the hydroxyl number of an intermediate, $$Y[(A)_n-H]_x \tag{II}$$

and the total average molecular weight of the copolymer is at least about 5000.

Preferred are polyoxyalkylene block copolymers of the formula:

$$HO(C_2H_4O)_b(C_4H_8O)_a(C_2H_3O)_bH \tag{III}$$

wherein in III, a is an integer such that the hydrophobe base represented by $(C_4H_8O)_a$ has a molecular weight of at least about 500 as determined by hydroxyl number, the polyoxyethylene chain constituting at least about 70% by weight of the copolymer, and the copolymer having a total average molecular weight of at least 15,000, or $$HO(C_2H_4O)_b(C_3H_6O)_a(C_2H_4O)_bH \tag{IV}$$

wherein in IV, a is an integer such that the hydrophobe base represented by $(C_3H_6O)_a$ has a molecular weight of at least about 900 average molecular weight, as determined by hydroxyl number, the polyoxyethylene chain constitutes at least about 70% by weight of the copolymer, and the copolymer having a total average molecular weight of at least about 15,000, or

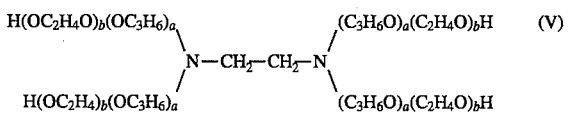

wherein in V, a and b are integers such that the copolymer has a hydrophobe molecular weight of at least about 1500, a hydrophile content of at least about 70%, and a total average molecular weight of at least about 15,000.

Most preferred are the polyoxyalkylene block copolymer, of the formula:

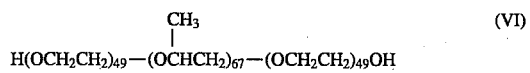

These polymers are present, preferably, in the amount of about 10 to about 30% by weight of the total weight of the compositions of the invention.

The pharmaceutical vehicles of the invention for drug delivery are an improvement over those prior art methods of drug delivery of the prior art in that the compositions are, preferably, optimized for tolerance in the eye, on the skin, in a body cavity, or for injection, preferably, by formulating the drug delivery compositions so as to have iso-osmotic (isotonic) characteristics in the gel state. Generally, the compositions of the invention also can be formulated to be hyper-isotonic or hypo-isotonic (hyper-osmotic or hypo-osmotic) in the gel state. By matching the osmolality of the drug delivery compositions of the invention, for instance, to those of bodily fluids such as the lacrimal fluid of the eye, it is possible to eliminate burning or other discomfort upon application of the drug delivery systems of the invention to the eye, to the skin, in a body cavity, or by injection. Drugs or diagnostic agents which can be administered to the eye of a mammal by means of the compositions according to the invention are, for example: antibacterial substances such as beta-lactam antibiotics, such as cefoxitin, n-formanidolthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides; aminoglycoside antibiotics such as gentamycin, kanamycin, amikacin, sisomicin and tobramycin; nalidixic acid and its analogs such as norfloxacin and the antimicrobial combination fluoroalanine/pentizidone, nitrofurazones and analogs thereof; antihistaminics and decongestants such as pyrilamine, chlorpheniramine, tetrahydrazoline, antazoline and analogs thereof; mast-cell inhibitors of histamine release, such as cromolyn; anti-inflammatories such as cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indomethacin, sulindac, its salts and its corresponding sulfides, and analogs thereof; miotics and anticholinergics such as echothiophate, pilocarpine, physostigmine salicylate, diisopropylfluorophosphate, epinephrine, dipivalopylepinephrine, neostigmine, echothiopate iodide, demecarium bromide, carbamoyl choline chloride, methacholine, bethanechol, and analogs thereof;

mydriatics such as atrophine, homatropine, scopolamine, hydroxyamphetamine, ephedrine, cocaine, tropicamide, phenylephrine, cyclopentolate, oxyphenonium, eucatropine, and analogs thereof;

Other drugs can be used in the treatment of conditions and lesions of the eyes such as:

antiglaucoma drugs, for example, timolol, and especially its maleic salt and R-timolol and a combination of timolol or R-timolol with pilocarpine, as well as many other adrenergic agonists and/or antagonists: epinephrine and an epinephrine complex, or prodrugs such as bitartrate, borate, hydrochloride and dipivefrine derivatives; carbonic anhydrase inhibitors such as acetazolamide, dichlorphenamide, 2-(p-hydroxyphenyl)-thio thiophenesulfonamide, 6-hydroxy-2-benzothiazolesulfonamide, and 6-pivaloyloxy-2-benzothiazolesulfonamide;

antiparasitic compounds and/or anti-protozoal compounds such as ivermectin, pyrimethamine, trisulfapidimidine, clindamycin and corticosteroid preparations;

compounds having antiviral activity such as acyclovir, 5-iodo-2'-deoxyuridine (IDU), adenosine arabinoside (Ara-A), trifluorothymidine, interferon, and interferon-inducing agents such as poly I:C;

antifungal agents such as amphotericin B, nystatin, flucytosine, natamycin and miconazole;

anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine; ophthalmic diagnostic agents, such as:

(a) those used to examine the retina such as sodium fluorescein;

(b) those used to examine the conjunctiva, cornea and lacrimal apparatus, such as fluorescein and rose bengal; and (c) those used to examine abnormal pupillary responses such as methacholine, cocaine, adrenaline, atropine, hydroxyampnetamine and pilocarpine;

ophthalmic agents used as adjuncts in surgery such as alpha chymotrypsin and hyaluronidase;

chelating agents such as ethylenediaminetetraacetic acid (EDTA) and deferoxamine;

immunosuppressants and anti-metabolites such as methotrexate, cyclophosphamide, 6-mercaptopurine and azathioprine and combinations of the compounds mentioned above, such as antibiotics/antiinflammatories combinations such as the combination of neomycin sulfate and dexamethasone sodium phosphate and combinations concomitantly used for treating glaucoma, for example, a combination of timolol maleate and aceclidine.

With specific reference to the use of the pharmaceutical compositions of the invention for administration to the skin of a mammal, it is contemplated to use suitable medicaments such as antibacterial substances, anti-infectives, anesthetics, anti-inflammatories, anti-parasitics, antivirals, antifungals, analgesics, and diagnostics. Representative antibacterial substances are the antibacterial substances selected from the group consisting of beta-lactam antibiotics, tetracyclines, chloramphenicol, neomycin, gramicidin, bacitracin, sulfonamides, aminoglycoside antibiotics, tobramycin, nitrofurazone, nalidixic acid and analogs, the antimicrobial combination of fludalanine/pentizdone, mafenide acetate, silver sulfadiazine, and nitrofurazone. Representative beta-lactam antibiotics or representative anti-infectives areiodine, chloramines, benzalkonium chloride and phenol, representative anti-inflammatory drugs are cortisone, hydrocortisone, betamethasone, dexamethasone, fluocortolone, prednisolone, triamcinalone, indomethacine, sulindac and its salts and corresponding sulfide. A representative antiparasitic drug is ivermectin. Representative antiviral drugs are acyclovir and interferon. Representative anesthetic drugs are benzocaine, lidocaine and dibucaine. Representative antifungal drugs are tolnaftate, undecylenic acid, salicylic acid, zinc undecylenate miconazole, and thiabendazole. Representative analgesic drugs are methylsalicylate, menthol, camphor, methylnicotinate, triethanolamine salicylate, glycol salicylate and salicylamine. Representative diagnostic compounds are n-alkyl carbonates, cholesteryl oleyl carbonate, cholesteryl nonanoate or cholesteryl benzoate all in proper proportions to effect liquid crystal responses.

With respect to the use of the pharmaceutical compositions of the invention for injection either subcutaneously or intramuscularly, the following classes of drugs selected from the group consisting of antibacterial substances, antihistamines and decongestants, anti-inflammatories, antiparasitics, antivirals, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, antihypertensives and muscle relaxants. Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid and analogs and the antimicrobial combination of fludalanine/pentizidone. Representative antihistamines and decongestants are perilamine, chlorpheniramine, tetrahydrozoline and antazoline. Representative antiinflammatory drugs are cortisone, hydrocortisone, betamethasone, dexamethasone, fluocortolone, prednisolone, triamcinolone, indometnacin, sulindac and its salts and corresponding sulfide. A representative antiparasitic compound is ivermectin. Representative antiviral compounds are acyclovir and interferon. Representative analgesic drugs are diflunisal, aspirin or acetaminophen. Representative antiarithritics are phenylbutazone, indomethacin, sulindac, its salts and corresponding sulfide, dexamethasone, ibuprofen, allopurinol, oxyphenbutazone or probenecid. Representative antiasthma drugs are theophylline, ephedrine, beclomethasone dipropionate and epinephrine. Representative anticoagulants are heparin, bishydroxycoumarin, and warfarin. Representative anticonvulsants are diphenylhydantoin and diazepam. Representative antidepressants are amitriptyline, chlordiazepoxide perphenazine, protriptyline, imipramine and doxepin. Representative antidiabetics are insulin, somatostatin and its analogs, tolbutamide, tolazamide, acetohexamide and chlorpropamide. Representative antineoplastics are adriamycin, fluorouracil, methotrexate and asparaginase. Representative antipsychotics are prochlorperazine, lithium carbonate, lithium citrate, trioridazine, molindone, fluphenazine, trifluoperazine, perphenazine, amitriptyline and triflupromazine. Representative antihypertensives are spironolactone, methyldopa, hydralazine, clonidine, chlorothiazide, deserpidine, timolol, propranolol, metoprolol, prazosin hydrochloride and reserpine. Representative muscle relaxants are succinylcholine-chloride. danbrolene, cycloenzaprine, methocarbamol and diazepam.

Many pharmaceutically active materials may be delivered to body cavities by the drug delivery system of this invention. Preferably, the drug or pharmaceutical, is water soluble. Some drugs will show greater solubility in the aqueous polymer system than others. Cosolvents can be used to enhance drug solubility, however, some drugs may be insoluble. These can often be suspended in the polymer vehicle with the aid of suitable suspending or viscosity-enhancing agents.

Suitable classes of drugs which can be administered to a body cavity (such as the rectum, urethra, nasal cavity, vagina, auditory mears, oral cavity, buccal pouch, peritoneium, or pleura) by the drug polymer delivery system of the present invention are antibacterial substances such as B-lactam antibiotics, such as cefoxitin, n-formamidoyl thienamycin and other thienamycin derivates, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fludalanine/pentizidone; nitroflurazones, and the like; antihistaminics and decongestants such as pyrilamine, cholphenriamine, tetrahydrazoline, antazoline, and the like; anti-inflammatories such as cortisone, hydrocortisone, betamethasone, dexamethasone, fluocortolone, pednisolone, triamcinolone, indomethacin, sulindac, its salts and its corresponding sulfide, and the like. Also included are antiparasitic compounds such as ivernectin; antiviral effective compounds such as acyclovir and interferon.

For treatment of vaginal and urethral conditions requiring antifungal, amoebicidal, trichomonacidal agents or; antiprotozoals, the following agents can be used: polyoxyethylene nonylphenol, alkylaryl sulfonate, oxyquinoline sulfate, miconazole nitrate, sulfanilamide, candicidin, sulfsoxazole, nystatin, clotrimazole, metronidazole and the like and antiprotozoals such aschloramphenicol, chloroquine, trimethoprim, sulfamethoxazole and the like.

For use rectally the following suitable drugs can be administered by the drug polymer delivery system of the present invention:

(1) Analgesics such as aspirin, acetaminophen, defunisal and the like.

(2) Anesthetics such as lidocaine, procaine, benzocaine, xylocaine and the like.

(3) Antiarthritics such as phenylbutazone, indomethacin, sulindac, dexamethasone, ibuprofen, allopurinol, oxyphenbutazone probenecid and the like.

(4) Antiasthma drugs such as theophylline, ephedrine, beclomethasone dipropionate, epinephrine and the like.

(5) Urinary tract disinfectives such as sulfamethoxazcle, trimethoprim, nitrofurantoin, norfloxicin and the like.

(6) Anticoagulants such as heparin, bis-hydroxy coumarin, warfarin and the like.

(7) Anticonvulsants such as diphenylhydantoin, diazepam and the like.

(8) Antidepressants such as amitriptyline, chlordiazepoxide, perphenazine, protriptyline, imipramine, doxepin and the like.

(9) Antidiabetics such as insulin, tolbutamide, tolazamide, acetohexamide, chlorpropamide and the like.

(10) Antineoplastics such as adriamycin, flurouracil, methotrexate, asparaginase and the like.

(11) Antipsychotics such as prochlorperazine, lithium carbonate, lithium citrate, thioridazine, molindone, fluphenazine, trifluoperazine, perphenazine, amitriptyline, trifluoromazine and the like.

(12) Antihypertensive such as spironolactone, methyldopa, hydralazine, clonidine, chlorothiazide, deserpidine, timolol, propranolol, metoprolol, prazosin hydrochloride, reserpine and the like, and

(13) Muscle relaxants such as mephalan, danbrolene, cyclobenzaprine, methocarbamol, diazepam and the like.

(14) Antiprotozoals such as chloramphenicol, chloroquine, trimethoprim and sulfamethoxazole.

(15) Spermicidals such as nonoxynol-9.

The particular drug used in the pharmaceutical composition of this invention is the type which a patient would require for pharmacological treatment of the condition from which said patient is suffering. For example, if the patient is suffering from pain or itch of the external auditory canal, the drug of choice would probably be benzocaine.

Also included in this invention is the use of the drug delivery device or pharmaceutical composition minus the active drug, diagnostic agent, or medicament for restoration or maintenance of vaginal acidity. All the ratios of components as described above would be satisfactory for this composition. For this use one would administer the vehicle as needed at the desired osmolality and pH.

In general the drug delivery system of the present invention will contain from about 0.01% to about 60% by weight of the medicament or pharmaceutical, from about 10 to about 50% of the polymer and from 80% to about 20% water. In special situations, however, the amounts may be varied to increase or decrease the dosage schedule.

If desired, the drug delivery vehicle may also contain preservatives, cosolvents, suspending agents, viscosity enhancing agents, ionic-strength and osmolality adjustors and other excipients in addition to the medicament and buffering agents. Suitable water soluble preservatives which may be employed in the drug delivery vehicle are sodium bisulfite, sodium thiosulfate, ascorbate, benzalkonium chloride, chlorabutanol, thimerosal, phenylmercuric borate, parabens, benzylalcohol phenylethanol and others. These agents may be present, generally, in amounts of about 0.001% to about 5% by weight and, preferably, in the amount of about 0.01 to about 2% by weight.

Representative buffering agents or salts useful in maintaining the pH at about 7.4+0.2 are alkali or alkaline earth metal carbonates, chlorides, sulfates, phosphates, bicarbonates, citrates, borates, acetates and succinates such as sodium phosphate, citrate, borate, acetate, bicarbonate, carbonate and tromethamine (TRIS). These agents are present in amounts sufficient to maintain the pH of the system at 7.4+0.2 and preferably, 7.4. As such, the buffering agent can be as much as 5% on a weight basis of the total composition.

The preparation of the pharmaceutical drug delivery compositions of the invention is described below. The Examples which follow were prepared according to the following preparation procedure. Since the polymer systems of this invention dissolve more completely at reduced temperatures, the preferred method of solubilization (cold process) is to start by adding the required amount of polymer to the amount of cold water to be used. Generally after wetting the polymer by shaking, the mixture is capped and placed in a cold chamber or in a thermostatic container at about 0° C. to 10° C. in order to dissolve the polymer. The mixture can be stirred or shaken to bring about a more rapid solution of the polymer. The pharmacologically active medicaments and various additives such as buffers, salts, and preservatives can subsequently be added and dissolved. In some instances, the pharmacologically active substance must be suspended since it is insoluble in water.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

This Example formulation describes a composition of the invention for opthalmic use as a surgical aid. The composition prepared was characterized as iso-osmotic, sterile, and having a pH of 7.4+0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC® F-127 (also known as Poloxamer 407) by the BASF Corporation, Parsippany, N.J. A solution in TRIS hydrochloride buffer was made by dissolving said polymer in cold (4° C.) buffer to give a concentration of 25% by weight in accordance with the cold process procedure described above for forming aqueous solutions. More specific solution procedures are described in "Artificial Skin I Preparation and Properties of PLURONIC F-127 Gels For Treatment of Burns", *Journal of biomedical material research* 6, 527, 1972, incorporated herein by reference. The block copolymer has the formula:

$$H[OCH_2CH_2]_{49}[OCH\ CH_2]_{67}[OCH_2CH_2]_{49}OH \qquad (VI)$$

This formulation forms the basis for the FIGURE in which curve A is the determined osmolality of the formulation in the liquid state and curve B is the calculated osmolality of the formulation in the gelled state, assuming the gelled molecules of the Poloxamer 407 no longer contribute to the osmotic forces. It is noted that generally the formulation will gel at mammalian body temperatures only at concentrations of polymer exceeding 17%.

The formulation was sterilized by autoclaving at 121° C. and 15 psi for 15 minutes. The pH before autoclaving was found to be 7.3 and after autoclaving remained the same. The osmolality in the gelled state before autoclaving was determined to be 290+10 and after autoclaving 298+10 mOsm/Kg. The gel strength (viscosity) in centipoise, as measured at 37 degrees C. using a Brookfield (spindle and cup) viscometer at 20 revolutions per minute, was greater than 44,000 before autoclaving and greater than 44,000 after autoclaving.

EXAMPLE 2

This example formulation describes an iso-osmotic, isotonic, pH balanced, thermoreversible system, in which the active ingredients are dissolved. The following antibiotic formulation was prepared to contain 3.5 mg. of neomycin sulfate and 10,000 units of polymyxin B sulfate per gram of antibiotic formulation solution. The antibiotic formulation was prepared as follows:

| INGREDIENT | PERCENT BY WEIGHT |
|---|---|
| Neomycin sulfate | 0.55 |
| Polymyxin B sulfate | 0.12 |
| Glycerin | 0.7 |
| Poloxamer 407 (BASF) | 19.0 |
| Methyl Propyl Parabens (9:1) | 0.1 |
| TRI hydrochloride buffer (0.1 molar) | 79.53 |

The formulation was prepared by dissolving the methyl/propyl paraben preservative, neomycin sulfate and polymyxin B sulfate by stirring in the required amount of TRIS hydrochloride buffer. These ingredients were placed in a glass beaker on ice and the Poloxamer 407 was added to the beaker slowly while stirring. After the Poloxamer 407 was completely dissolved, the formulation was stored at 4° C. The product obtained was characterized as clear, colorless and exhibiting gellation at the temperature of mammalian skin (33+2° C.). The formulation was sterilized by autoclaving for 15 minutes at 15 psi and 121° C. The pH and osmolality of the product were as follows: pH 7.5 and osmolality of approximately 650 mOsm/Kg in the liquid state. In the gelled state, the pH and osmolality of the preparation would be expected to be 7.5 and 290 mOsm/Kg respectively.

EXAMPLE 3

This is an example of an iso-osmotic, isotonic, pH balanced, thermoreversible system, in which the active ingredient is dispersed.

The following antibacterial formulation was prepared to contain one percent by weight of silver sulfadiazine.

| INGREDIENT | PERCENT BY WEIGHT |
|---|---|
| Silver Sulfadiazine | 1.0 |
| Glycerin | 0.25 |
| Xanthan Gum | 0.33 |
| Poloxamer 407 (BASF) | 18.66 |
| Methyl/Propyl Parabens (9:1) | 0.1 |
| TRIS Maleate Buffer (0.05 molar) (0.1 molar) | 79.72 |

The formulation was prepared by levigating silver sulfadiazine and glycerin in a glass mortar. A weighed amount of xanthan gum paste (2.5% in a buffer portion) was added with continued levigation. The Poloxamer 407 and the methyl/propyl paraben preservatives were added to the other buffer portion, in accordance with the cold process described above, to prepare an aqueous solution. This solution was weighed and mixed with a weighed amount of levigated mix. The mixing was achieved using a homogenizer under a nitrogen environment. The product obtained was characterized as milky-white and exhibiting gellation at the temperature of mammalian skin (33+2° C.). The pH of the product was 7.32 and the measured osmolality in the liquid state was 573 mOsm/Kg. The calculated osmolality in the gelled state was approximately 290 mOsm/Kg.

EXAMPLES 4 and 5

Examples 2 and 3 are repeated substituting 21% by weight of polymer #2, as described in U.S. Pat. No. 4,810,503 and 4% by weight of surfactant #1, as described therein.

The balance of the percentage of Poloxamer 407 used in Examples 2 and 3 is made up with TRIS hydrochloride buffer. These formulations form gels at room temperature. Substantially similar pH and osmolality results are obtained.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

What is claimed is:

1. A method for making a pharmaceutical carrier, where said carrier is a gel with a desired osmolality at mammalian body temperature, comprising:

(a) providing in an aqueous solution containing a pharmaceutical agent and a surfactant and a polyalkylene polyether, said surfactant and said polyalkylene polyether being present in a combined total amount not exceeding about 10% by weight, said polyether having a molecular weight of about 5,000 to about 100,000, wherein said polyether is selected from the group consisting of (A) polyoxyalkylene polyethers prepared by reacting ethylene oxide and at least one lower alkylene oxide having 3 to 4 carbon atoms with at least one active hydrogen-containing compound having form 3 to 10 carbon atoms and from 3 to 6 active hydrogens to prepare a heretic or block copolymer intermediate and further reacting said copolymer intermediate with at least one alpha-olefin oxide having an average carbon chain length of about 20 to 45 aliphatic carbon atoms and wherein said alpha-olefin oxide is present in the amount of about 0.1 to 10 percent by weight based upon the total weight of said polyether or (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.1 to 10 percent by weight based on the total weight of the polyether, and (b) adjusting the osmolality of the aqueous solution to a predetermined level to achieve the desired value of the osmolality of the gel by assuming that the polyoxyalkylene polyether does not contribute to the osmolality of the gel.

2. The method according to claim 1 wherein said aqueous solution of capped polyether polyols includes an ionic or non-ionic surfactant.

* * * * *

UNITED STATES PATENT AND TRADEMARK OFFICE
CERTIFICATE OF CORRECTION

PATENT NO. : 5,593,683
DATED : January 14, 1997
INVENTOR(S) : Tacey X. Viegas, Lorraine E. Reeve, Raymond L. Henry It is certified that error appears in the above-identified patent and that said Letters Patent is hereby corrected as shown below:

Column 2, line 9, "kpro" should be --pro--.

Signed and Sealed this

Ninth Day of December, 1997

Attest:

BRUCE LEHMAN

Attesting Officer

Commissioner of Patents and Trademarks